Figure 1A:
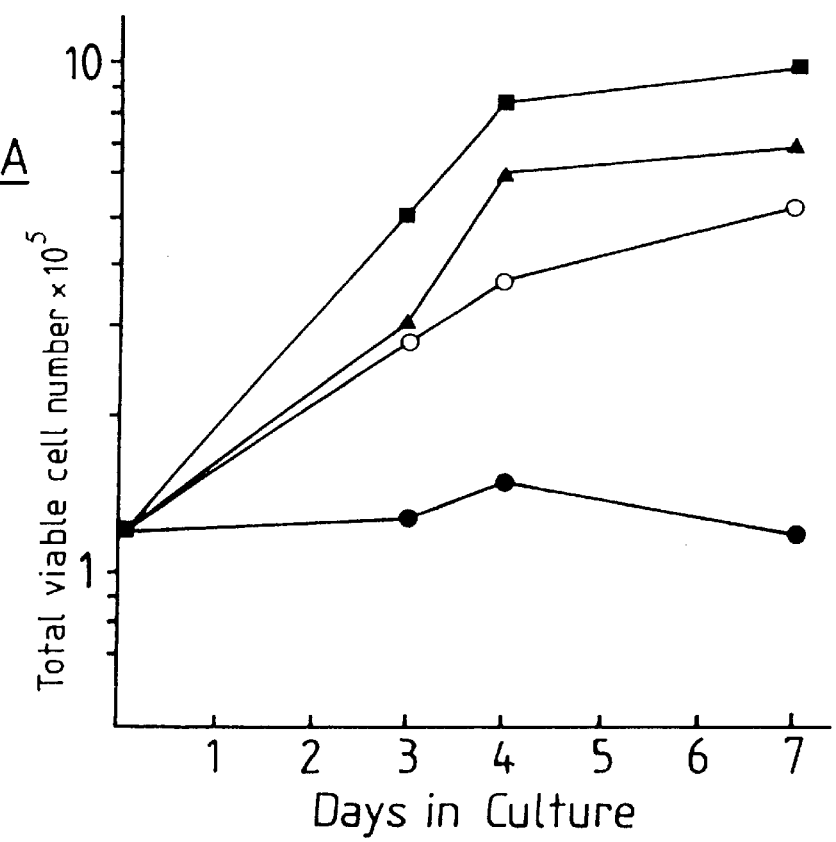

United States Patent
Nagley et al.

[11] Patent Number: 5,981,601
[45] Date of Patent: *Nov. 9, 1999

[54] METHOD FOR ENHANCING CELLULAR BIOENERGY

[75] Inventors: Phillip Nagley, South Caulfield; Anthony William Linnane, Canterbury; Ryan Dennis Martinus, Armadale; Francois Vaillant, Sunshine, all of Australia

[73] Assignee: Centre for Molecular Biology and Medicine, Victoria, Australia

[ * ] Notice: This patent issued on a continued prosecution application filed under 37 CFR 1.53(d), and is subject to the twenty year patent term provisions of 35 U.S.C. 154(a)(2).

[21] Appl. No.: 08/343,559

[22] PCT Filed: May 28, 1993

[86] PCT No.: PCT/AU93/00251
§ 371 Date: Mar. 20, 1995
§ 102(e) Date: Mar. 20, 1995

[87] PCT Pub. No.: WO93/24650
PCT Pub. Date: Dec. 9, 1993

[30] Foreign Application Priority Data

May 28, 1992 [AU] Australia ................................ 2641/92
May 28, 1992 [AU] Australia ................................ 2642/92

[51] Int. Cl.⁶ .................................................. A61K 31/12
[52] U.S. Cl. ............................................. 514/690; 514/675
[58] Field of Search ..................... 552/293; 514/293, 514/307, 296, 675, 690

[56] References Cited

U.S. PATENT DOCUMENTS

| | | | |
|---|---|---|---|
| 3,705,239 | 12/1972 | Gregory | 424/166 |
| 4,436,753 | 3/1984 | Imada et al. | 424/331 |
| 4,491,594 | 1/1985 | Ogawa et al. | 424/331 |
| 4,599,232 | 7/1986 | Bertelli | 424/94 |
| 5,227,405 | 7/1993 | Fridovich et al. | 514/612 |
| 5,281,628 | 1/1994 | Hlavka et al. | 514/510 |
| 5,460,819 | 10/1995 | Gallop et al. | 514/292 |

FOREIGN PATENT DOCUMENTS

| | | |
|---|---|---|
| 0 146 742 | 7/1985 | European Pat. Off. . |
| 0 243 849 | 11/1987 | European Pat. Off. . |
| WO 92/03052 | 3/1992 | WIPO . |
| WO 92/17173 | 10/1992 | WIPO . |

OTHER PUBLICATIONS

R.A. Morton, "Biochemistry of Quinones", 1965, pp. 1–3, 7, 43, 105–107, 150, 196–198 and 210.
Alberts et al., "Molecular Biology of the Cell", 1983, pp. 490–500.
Advances in Human Genetics, 19, 1990, 308–313.
Linnane, et al. "Mitochondrial DNA Mutations as an Important Contributor to Ageing and Degenerative Diseases", The Lancel, Mar. 25, 1989, pp. 642–645.
Patent Abstract of Japan, 13, No. 247(c–639), 22.9.89.
F.L. Crane et al., (1991), "Electron and Proton Transport Across the Plasma Membrane," *J. Bioenergetics and Biomembranes,* 23(5):773–803.
F.L. Crane et al., (1985), "Transplasma–Membrane Redox Systems in Growth and Development," *Biochimica et Biophysica Acta,* 811:233–264.
M.P. King et al., (1989), "Human Cells Lacking mtDNA" Repopulation with Exogenous Mitochondria by Complementation, *Science,* 246:500–503.
L. Lamperth et al., (1991), "Abnormal Skeletal and Cardiac Muscle Mitochondria Induced by Zidovudine (AZT) in Human Muscle In Vitro and in an Animal Model," *Laboratory Investigation,* 65(6):742–751.
L.A. Mulieri et al., (1989), "Protection of Human Left Ventricular Myocardium From Cutting Injury With 2,3–Butanedione Monoxime," *Circulation Research,* 65(5):1441–1444.
P. Tyle, (1986), "Iontophoretic Device for Drug Delivery," *Pharmaceutical Research,* 3(6):318–326.

*Primary Examiner*—Jose' G. Dees
*Assistant Examiner*—Barbara Badio
*Attorney, Agent, or Firm*—Scully, Scott, Murphy & Presser

[57] ABSTRACT

The present invention relates generally to therapeutic compositions comprising one or more redox compounds. The therapeutic compositions of the present invention are useful in enhancing cellular ATP production thereby ameliorating the effects of reduced bioenergy capacity such as occurring during aging, systemic or vascular disease or in conjunction with chemical therapy. The present invention therefore contemplates a method for enhancing cellular ATP production in an animal, said method comprising administering to said animal, an effective amount of a redox compound for a time and under conditions sufficient to increase or otherwise elevate the activity and/or operation of a cellular oxidoreductase system in cells of said animal.

25 Claims, 6 Drawing Sheets

METHOD FOR ENHANCING CELLULAR BIOENERGY

This application is a 371 of PCT/AU 93/00251 filed May 28, 1993.

The present invention relates generally to therapeutic compositions comprising one or more redox compounds. The therapeutic compositions of the present invention are useful in enhancing cellular ATP production thereby ameliorating the effects of reduced bioenergy capacity such as occurring during aging, systemic or vascular disease or in conjunction with chemical therapy.

Cells unable to meet their biological energy (bioenergy) demand from intracellular produced ATP become non-functional and generally die. The bioenergy threshold is different for various cell types and tissues of the body. For example, brain, skeletal muscle and cardiac muscle have a high oxygen demand and are highly dependent on mitochondrial oxidative phosphorylation. Other tissues with lower bioenergetic demand contain comparatively few mitochondria and rely to a greater extent on glycolysis as a source of ATP.

The two basic mechanisms responsible for cellular ATP production are cytosolic glycolysis and mitochondrial respiration. ATP synthesis via glycolytic processes involves the oxidation of glucose to pyruvate, coupled to the reduction of $NAD^+$ to NADH. In order for this pathway to be maintained, the supply of $NAD^+$ must continually be regenerated through a redox sink. For example, in muscle tissue the re-oxidation of NADH can be achieved by the conversion of pyruvate to lactate by lactate dehydrogenase. In this case muscle lactate may be regarded as a redox sink for that tissue. ATP production by oxidative phosphorylation in functionally respiring mitochondria is integrated with the re-oxidation of NADH via the activity of the electron transport system In this case a supply of reduced pyridine nucleotides is needed. In addition to NADH generated by glycolysis, further amounts of "reducing power" (both pyridine and flavin nucleotides) are generated by the activities of the TCA cycle as well as oxidation of fatty acids in mitochondria. Another significant cell system involved in the maintenance of cellular $NAD^+$/NADH redox balance is the plasma membrane oxidoreductase enzyme system (Crane et al, *J. Bioenergy Biomember* 23, 773–803, 1991). In cases where the mitochondrial electron transport chain is impaired (such as in mitochondrial disease and the ageing process), a decline in ATP production and under certain conditions concomitant build up of NADH is proposed to ensue. The metabolic consequence of such mitochondrial dysfunction would be an increasing reliance by the cell on cytosolic glycolysis to generate the ATP required for cellular maintenance and growth, acting in concert with the plasma membrane NADH oxidoreductase system. A key feature of cellular bioenergetics is, therefore, the balance that must be maintained between the oxidised and reduced forms of these nucleotide co-enzymes (exemplified by the $NAD^+$/NADH ratio), by the interaction of the glycolytic pathway, mitochondrial respiratory and plasma membrane oxidoreductase enzyme system.

Cells may become unable to meet their bioenergy threshold as a result of mitochondrial poisons which directly or indirectly disrupt mitochondrial respiratory chain function; certain degenerative diseases which are caused by mutations in mitochondrial DNA (mtDNA); and aging which may result in a high rate of somatic gene mutation in the mtDNA. The mitochondrial genome is subjected to a high mutation rate mainly because of its close proximity to the major source of cellular free radicals (the mitochondrial electron transport chain) and because the mitochondrial organelle lacks an efficient DNA repair system. The mitochondrial genome (16,569 bp) essentially encodes only genes concerned with energy production. It contains the structural genes for seven proteins of complex I of the respiratory chain, a single sub-unit protein of complex III, three sub-units of complex IV and two sub-units of ATP synthase (complex V); the rest of the mitochondrial DNA codes for the organellar rRNA's and tRNA's specific to mitochondrial protein synthesis. Given the paucity of spacer regions between mammalian and human mitochondrial genes, a mutation of the mtDNA will be almost certain to involve a functionally important region of the genome with implications of a possible effect on cellular bioenergy processes.

In work leading up to the present invention, the inventors discovered that a variety of redox compounds can replace pyruvate in order to achieve the end point requirements of generating cytosolic $NAD^+$. This work establishes a key role for the interaction between the plasma membrane oxidoreductase and glycolysis in enabling the viability and growth of mitochondrially compromised cells which will exhibit reduced bioenergy capacity. This condition is known as "bioenergetic disease" and is associated inter alia with aging, systemic and vascular disease and in some chemical therapy. With regards to the latter, chemical therapy is commonly used, for example, in treating viral and in particular retroviral infection such as infection by human immunodeficiency virus (HIV). HIV infection progresses through various stages of increasing severity after an initial latency period. The virus causes immune deficiency by destroying a sub-set of human T-lymphocytes (helper T-cells) which are involved in establishing an immune response. Zidovudine (AZT) is the drug of choice in the treatment of HIV infection While AZT is relatively effective in treating HIV infection, it cannot be regarded as an innocuous compound. AZT, metabolic products thereof, or impurities therein, cause a number of side effects which limit long term treatment with the drug. AZT exhibits cellular cytotoxicity which is particularly manifest in muscle, causing a myopathy. The AZT induced myopathy is characterised by myalgia, muscle weakness and elevation of serum creatine kinase (Lamperth et al, *Lab. Inv.* 65 (6) 742–730, 1991). HIV may also produce a muscle myopathy similar to that induced by AZT. The cellular cytotoxicity of AZT may in part be due to its ability to act as a mitochondrial poison and adversary affecting mitochondrial chain function.

There is a need, therefore, for a method of ameliorating the loss of cellular capacity to generate ATP whatever the causative mechanism thereby ameliorating the effects of reduced bioenergy capacity. The present invention is particularly useful, therefore, in ameliorating the effects of bioenergetic disease.

Accordingly, one aspect of the present invention contemplates a method for enhancing cellular ATP production in cells of an animal said method comprising administering to said animal of an effective amount of a redox compound for a time and under conditions sufficient to increase or otherwise elevate the activity and/or operation of a cellular oxidoreductase system in cells of said animal Optionally, an anti-oxidant and/or uridine (including functional derivatives and/or precursors thereof) is/are also administered. Examples of oxidoreductase systems include mitochondrial electron transport systems.

The "effective amount" of the redox compound is an amount of redox compound capable of increasing or otherwise elevating the activity and/or operation of one or more cellular oxidoreductase systems in the animal cell. A single redox compound may be administered or multiple compounds may be given either simultaneously or sequentially. The animal is preferably a mammal such as a human, livestock animal (e.g. horse, cow, sheep or goat), laboratory test animal (e.g. mouse, rat, rabbit or guinea pig), companion animal (e.g. cat or dog) or a captive or free wild animal. Most preferably, the animal is a human.

This aspect of the present invention is particularly directed to ameliorating the effects of reduced bioenergy capacity such as associated with aging, systemic or vascular disease or chemical therapy.

Another aspect of the present invention is directed to a method for ameliorating cytotoxic or otherwise adverse effects of anti-viral therapy in an animal using an anti-retroviral agent, said method comprising the sequential or simultaneous administration of a redox compound with said anti-retroviral agent. Optionally, an anti-oxidant and/or uridine (including functional derivatives and/or precursors thereof) is/are also administered.

The "animal" is generally as defined above and is most particularly a human. The effective amount of the redox compound is that required to prevent, reduce or otherwise ameliorate the cytotoxic side effects of the anti-viral therapy. Preferably, the effective amount of redox compound is that amount required to increase or otherwise elevate the activity and/or operation of a cellular oxidoreductase system in the animal cell.

Anti-retroviral agents include a range of molecules and chemical compounds capable of inhibiting viral adsorption, replication and/or other stages in the retrovirus life cycle. In a preferred embodiment, the anti-viral agent is AZT or 3'-amino-3'-deoxythymidine (AMT). The cytotoxic effects may be by AZT or AMT directly or by metabolites thereof or contaminants therein.

By "sequential or simultaneous administration" is meant a therapeutic regime involving both the redox compound and the anti-retroviral agent. Sequential administration occurs when, in either order, both compounds are not co-administered in the same composition. For example, the redox compound may be administered orally and the anti-retroviral compound may be administered intravenously. Alternatively, both compounds are administered by the same route but at different times with an appropriate interval ranging from seconds, minutes, hours, days or weeks. Sequential administration extends to the single administration of, for example, the redox compound and the multiple administration of the anti-retroviral, compound.

A further aspect of the present invention provides a pharmaceutical composition comprising a therapeutically effective amount of a redox compound and an anti-oxidant together with one or more pharmaceutically acceptable carriers and/or diluents. The anti-oxidant scavengers free oxygen radicals and include, but are not limited to, Vitamin E, carotenoids, Vitamin C and compounds with isoprenoid side chains such as coenzyme $Q_{10}$ and coenzyme $Q_6$. An isoprenoid side chain may be represented as

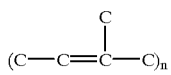

where n is 1 to 40, preferably 1 to 20 and more preferably 1 to 10. In $Q_{10}$, n is 10 and in $Q_6$, n is 6.

Yet another aspect of the present invention is directed to a pharmaceutical composition comprising a therapeutically effective amount of a redox compound and an anti-retroviral agent, together with one or more pharmaceutically acceptable carriers and/or diluents. Generally, the anti-retroviral compound is AZT or AMT.

This composition may also comprise an anti-oxidant as hereinbefore described Both of the aforementioned compositions may also contain uridine or functional derivatives thereof and/or a suitable precursor thereto (for example, orotic acid).

The term "redox compound" as used herein refers to one or more compounds capable of undergoing reduction and oxidation reactions and capable of recycling between a reduced and oxidised state.

Suitable redox compounds in accordance with the present invention include compounds of Formula (I):

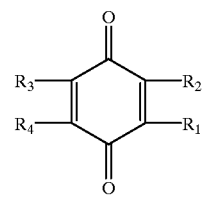

(I)

wherein $R_1$, $R_2$, $R_3$ and $R_4$ may be the same or different and each is H, $C_1$–$C_{10}$ alkyl, $C_1$–$C_{10}$ alkoxy, $C_2$–$C_{10}$ alkenyl, $C_2$–$C_{10}$ alkynyl, $C_3$–$C_{10}$ cycloalkyl, $C_1$–$C_{10}$ alkylthio, $C_1$–$C_{10}$ haloalkyl, phenyl, phenoxy, thiophenoxy, either not substituted or substituted with a substituent selected from the group consisting of halogen, $CC_1$–$C_6$ alkyl, $C_1$–$C_6$ alkoxy, alkylthio, amino, $C_1$–$C_6$ haloalkyl and $C_1$–$C_5$ haloalkoxy.

Preferably, $R_1$ is

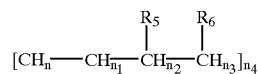

wherein each of n, $n_1$ and $n_2$ is 1 or 2; $n_3$ is 1–3; and $n_4$ is 0–40 where $R_5$ and $R_6$ may be the same or different and each is H, $C_1$–$C_{10}$ alkyl, $C_{1-C10}$ alkoxy, $C_2$–$C_{10}$ alkynyl, $C_3$–$C_{10}$ cycloalkyl, $C_1$–$C_{10}$ alkylthio, $C_1$–$C_{10}$ haloalkyl, phenyl, phenoxy, thiophenoxy, either not substituted or substituted from the list consisting of halogen, $C_1$–$C_6$ alkyl, $C_1$–$C_6$ alkoxy, alkylthio, amino, $C_1$–$C_6$ haloalkyl and $C_1$–$C_5$ haloalkoxy.

Preferably, the redox compounds include compounds of Formula (II):

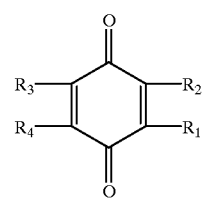

(II)

wherein
$R_2$ is H or methyl;
$R_3$ and $R_4$ are the same or different and each is methyl or methoxy; and

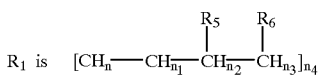

except wherein each of n, $n_1$ and $n_2$ is 1 or 2, $n_3$ is 2 or 3 and $R_5$ is $C_1$–$C_{10}$ alkyl, $C_1$–$C_{10}$ alkynl, $C_1$–$C_{10}$ alkoxy or $C_2$–$C_{10}$ alkenyl.

Even more preferably, the redox compound is a compound of Formula (III):

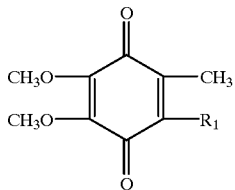

(III)

wherein $R_1$ is

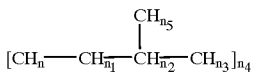

where n is 1 or 2; $n_1$ is 1 or 2; $n_2$ is 0 or 1; $n_3$ is 2 or 3; $n_4$ is 0–40; and $n_5$ is 2 or 3.

Alternatively, the redox compound is a compound of Formula (IV):

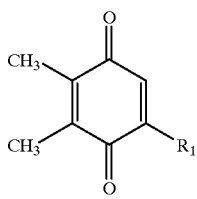

(IV)

where $R_1$ is

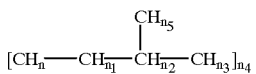

and $n_1$–$n_5$ are each as defined for Formula (III) above.

In a preferred embodiment, $n_4$ in compounds of Formulae (I)–(IV) is 0 to 20, more preferably 0 to 10 and even more preferably 6 to 10. In a most preferred aspect, $n_4$ is 10.

Other suitable redox compounds include optionally substituted benzoquinones, naphthoquinones and optionally substituted naphthoquinones (such as the vitamin K series), flavins (such as riboflavin), ascorbic acid and other reductic acids, organic redox substances, inorganic redox substances (such as potassium ferricyanide) and the like. Optional substituents may be selected from amino, nitro, halogen (e.g. F, Cl, Br, I) and straight or branched chain, alkyl or alkoxy groups, and the like.

A convenient assay for assessing activity of redox compounds in enhancing cellular ATP production involves incubating candidate compounds with mammalian cells which cannot synthesise ATP via mitochondrial oxidative phosphorylation (for example, so-called "$\rho^\circ$ cells" which are produced by culturing cells in the presence of ethidium bromide, King, M. P. and Attardi, G. *Science* 246: 500–503, 1989). Such cells can grow without mitochondrial respiratory function only when incubated with compounds which enhance cellular ATP production via non-mitochondrial respiratory systems (such as glycolysis). Alternatively, cells can be used with permanently or temporarily impaired mitochondrial electron transport/oxidative phosphorylation activity. An example of a temporarily impaired cell includes cells treated with AZT. All such cells, with totally or partially impaired mitochondrial electron transport/oxidative phosphorylation systems are referred to herein as having a reduced capacity for generating ATP. According to this aspect of the present invention there is provided a method for assaying for redox compounds capable of enhancing cellular ATP production, said method comprising incubating animal cells (e.g. mammalian cells) which exhibit a reduced capacity to synthesise ATP via oxidative phosphorylation with compounds to be tested for a time and under conditions sufficient for said cells to grow relative to a control, which control comprises cells which may remain dormant or die and then selecting compounds which promote growth of said cells. Preferably, the animal and redox compound are as hereinbefore described. Additionally, an antioxidant and/or uridine (including functional derivatives and/or precursors thereof) may be added to the test system.

In accordance with another aspect of this invention there is provided a method of assaying for redox compounds capable of enhancing cellular ATP production said method comprising incubating candidate compounds with mammalian cells which cannot synthesise ATP via oxidative phosphorylation and thereafter assessing survival of said cells as a measure of the capacity of compounds to enhance cellular ATP production and thereby upregulate bioenergy capacity of said cells.

Yet another aspect of the present invention contemplates a compound of Formulae (I)–(IV) or a benzoquinone, naphthoquinone, or flavin capable of acting as a redox compound or other redox compounds identified as determined by the above-mentioned method.

Still a further aspect of the present invention provides the use of a redox compound in the manufacture of a medicament for the enhancement of cellular ATP production and optionally with AZT or other anti-retroviral agent for amelioration of the cytotoxic effects of the anti-retroviral treatment An anti-oxidant amd/or uridine (including functional derivatives and/or precursors thereof) may also be used in the manufacture of the medicament.

The amount of a redox compound required to achieve the desired effects of enhancing cellular ATP and/or ameliorating the effects of anti-retroviral agents will depend upon a number of factors, and in particular, the specific application, the nature of the particular redox compound used, the mode of administration and the condition of the patient. In general, however, and without limitation to the present invention, a daily or weekly dose in the range of 100 µg to 5000 mg or more per patient per day is contemplated. A more preferred dose is 10 mg to 300 mg per patient per day.

The specific dosage of redox compounds administered will depend upon the condition being treated, the state of the subject and the route of administration as described above, but would typically be from 10 µg to 50 mg per kilogram of body weight per day and more preferably from about 100 µg to 15 mg per kilogram of body weight per day and even more preferably 1 mg to 10 mg per kilogram of body weight per day. Administration protocols and effective amounts may vary expecially if administered simultaneously or sequentially with an anti-retroviral compound. For example, multiple doses may be given every day or two days or on a weekly or monthly basis. Where the redox compound is admixed with AZT, 100 µg–2000 mg AZT may be required per patient per day, two days, week or month. A similar amount of AZT is used during sequential administration with the redox compound. Where uridine is also administered, an amount in the range of 100 µg to 2000 mg or more per patient per day is generally given.

In the manufacture of a medicament for the administration of redox compounds with or without one or more anti-retroviral compounds (e.g. AZT) in accordance with this invention, hereinafter referred to as a formulation, the redox compound with or without anti-retroviral compound is typically admixed with inter alia, one or more acceptable carriers and/or diluents. The carrier must, of course, be acceptable in the sense of being compatible with any other ingredients in the formulation and must not be deleterious to the patient. The carrier may be a solid or a liquid, or both, and is preferably formulated with a compound as a unit-dose formulation, for example, a tablet, which may contain from 0.5% to 95% by weight of the active compound. One or more active compounds may be incorporated in the formulations of the present invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), parental (e.g. subcutaneous, intramuscular, intradermal or intravenous) and transdermal administration, although the most suitable route in any given case will depend on the nature of the severity of the condition being treated and on the nature of the particular active compound which is being used.

Formulations suitable for oral administration maybe presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formations may be prepared by any suitable method of pharmacy which includes the step of bringing into association the active compound and a suitable carrier (which may contain one or more accessory ingredients as noted above). In general the formulations of the invention are prepared by uniformly and intimately admixing the active compound with a liquid or finely divided solid carrier and/or diluent, or both, and the, if necessary, shaping the resulting mixture. For example, a tablet may be prepared by compressing or moulding a powder or granules containing the active compound, optionally with one or more accessory ingredients.

Compressed tablets may be prepared by compressing, in a suitable machine, the compound in a free-flowing form, such as a powder or granules optionally mixed with a binder, lubricant, inert diluent, and/or surface active/dispersing agent(s). Moulded tablets may be made by moulding, in a suitable machine, the powdered compound moistened with an inert liquid binder. The tablets may also be incorporated into or be part of animal food such as various grains and the like.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Compositions of the present invention suitable for parental administration conveniently comprise sterile aqueous preparations of the active compounds, which preparations are preferably isotonic with the blood of the intended recipient. The preparations are preferably administered intravenously, although administration may also be effected by means of subcutaneous, intramuscular, or interdermal injection.

Such preparations may conveniently be prepared by admixing the compound with water or a glycine buffer and rendering the resulting solution sterile and isotonic with the bood. Injectable formulations according to the invention generally contain from 0.1 to 5% w/v active compound.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include vaseline, linoline, polyethylene glycols, alcohols, and combinations of two or more thereof. The active compound is generally present at a concentration of from 0.1 to 15% w/w, for example, from 0.5 to 2% w/w.

Formulations suitable for transdermal administration may be presented in discrete patches to remain in intimate contact with the epidermis of the recipient for a prolonged period of time. Such patches suitably contain the active compound as an optionally buffered aqueous solution of, for example, 0.1 to 0.2M concentration with respect to the said active compound.

Formulations suitable for transdermal administration may also be delivered by iontophoresis (see, for example, *Pharmaceutical Research* 3 (6), 318, 1986) and typically take the form of an optionally buffered aqueous solution of the active compound. Suitable formulations comprising citrate or bis/tris buffer (pH 6) or ethanol/water and contain from 0.1 to 0.2M active ingredient.

Compositions suitable for rectal, topical, buccal and transdermal administration may be prepared according to standard formulation procedures as are well known in the art and described for example in Remmington's Pharmaceutical Sciences (14th Edition, Hoover, T. E. et al, Eds. Mack Publishing Co., Easton, Pa., 1970).

The present inventors have shown that the cellular impermeable redox compound ferricyananide may be used to sustain the growth and viability of $\rho^\circ$ cells. The growth restorative action of ferricyanide is believed to be mediated by an NADH linked plasma membrane oxidoreductase that may encompass a plasma membrane NADH oxidase activity. Continuous restoration of appropriate intracellular $NAD^+$ levels is thus achieved by ferricyanide acting externally, this allows glycolysis to provide ATP for the growth of mitochondrially respiratory incompetent $\rho^\circ$ cells. Other redox compounds, whether permeable or impermeable to cells, may be utilised to enhance cellular ATP production by the plasma membrane oxidase system as well as other cellular oxidoreductase systems.

Cellular oxidoreductase systems, the activity of which may be increased in the presence of redox compounds, include the plasma membrane oxidase system as well as other cellular oxidoreductase systems.

The present invention is particularly directed to the amelioration of the effects of bioenergetic disease caused through, for example, aging, vascular or systemic disease or following chemical therapy.

Diseases associated with distruption of mitochondrial respiratory chain function include diseases resulting from mutations of mtDNA—such as Lebers disease, hereditary optic neuropathy and somatic mtDNA mutations which may result in encephalomyopathy lactic acidosis, stroke-like episodes, chronic progressive external ophthanlmoplegia, Kearns-Sayre syndrome, Pearson's marrow/pancreas syndrome and various cardiomyopathies). Other conditions treatable by the methods and compositions of the present invention include Parkinson's Disease and other neuromuscular diseases and Alzheimer's Disease. Vascular and systemic diseases also include cardiac conditions such as heart failure, strokes and diabetes. The redox compounds of the present invention may ameliorate the putative mitochondrial toxic effects of some anti-retroviral agents, such as AZT.

Accordingly, a further aspect of the present invention contemplates a method for the manufacture of a medicament for the treatment of HIV infection comprising an anti-retroviral agent and a redox compound optionally in association with a pharmaceutically acceptable carrier and/or diluent. Preferably, the anti-retroviral agent is AZT. An anti-oxidant and/or uridine may also be required.

In the manufacture of the medicament according to this invention, the redox compound and, for example, AZT are typically admixed with an acceptable carrier and/or diluent. The carrier and/or diliuent must be acceptable in the sense of being compatible with the other ingredients in the formulation and must not be deleterious to the patient. The carrier may be a solid or liquid, or both, and is preferably formulated with the compound as a unit-dose formulation for example a tablet which may contain from 0.5% to 95% by weight of the active compound.

In accordance with another aspect of this invention there is provided a method for ameliorating the cytotoxic effects of AZT which comprises administering to a subject in need of such treatment a therapeutically effective amount of AZT and a redox compound. Preferably, AZT and the redox compound are administered to a patient for the treatment of HIV infection.

AZT and a redox compound may be administered to a subject either (a) simultaneously in time (optionally by formulating the two components together in a common carrier) or (b) at different times during the course of a common treatment schedule. In the latter case, the two compounds are administered sufficiently close in time to achieve the intended therapeutic effects.

Where AZT and a redox compound are administered in the form of a single composition, formulations suitable for oral, rectal, topical, buccal, parenteral and transdermal administration may be prepared as previously described.

AZT may be administered in a manner and amount as is conventionally practised. Preferably, an effective amount of AZT comprises a daily dose of from 250 to 7000 mg or more, more preferably 500 to 1000 mg per day. An effective amount of a redox compound may comprise from 100 μg to 1000 mg or more per day, preferably 1 mg to 500 mg per day. It is to be understood that the amount of AZT or a redox compound administered to a patient is not limiting on this invention, but rather the method of this invention involves administering to a patient suffering, for example, from HIV infection, an amount of AZT which is therapeutically effective as part of an overall treatment schedule in the control of HIV infection, and an amount of a redox compound which is effective to ameliorate the cytotoxic effects of AZT, metabolites thereof (such as AMT) or impurities therein.

As conventional treatments with AZT involve daily doses of AZT over a prolonged time period, the methods of the present invention also involve long term daily administration (such as from 1 to 12 months or more) of an effective amount of AZT and a therapeutically effective amount of a redox compound.

AZT is a mitochondrial poison that affects the oxidation/phosphorylation system and the activity of complex I, III and IV of the mitochondrial respiratory chain by inhibiting the gamma-DNA polymerase of the mitochondrial matrix thereby effectively depleting mitochondria of gene products of the mitochondrial genome. AZT (and impurities and metabolites thereof) effects the capacity of cells to produce ATP which results in cellular dysfunction and also cell death.

The precise mechanism(s) by which redox compounds ameliorate the cytotoxic effects of AZT (or impurities or metabolites thereof) is uncertain. Without being limited to any particular theory or mode of action, the subject inventors believe that redox compounds may ameliorate the cytotoxic effects of AZT by one or more of (a) increasing the activity of plasma membrane and other cellular oxidase systems to produce $NAD^+$ (from NADH). $NAD^+$ may then drive glycolysis within cells to produce ATP; (b) redox compounds such as coenzyme $Q_{10}$ may assist in electron transport and oxidative phosphorylation within mitochondria to facilitate ATP production.

In another aspect of this invention there is provided a method for ameliorating the effects of mitochondrial poisons (such as AZT, nucleoside drugs, anti-tumour compounds, anti-bacterial and anti-viral compounds and the like) which comprises administering to a patient a therapeutically effective amount of a redox compound as herein described. The redox compound may be administered in conjunction with the mitochondrial toxin in the situation where the mitochondrial poisons possesses therapeutic benefits.

This aspect of the present invention is described hereinafter with reference to in vitro experiments where the effect of AZT on the growth of human cells in culture is investigated. This model provides a direct insight into the cellular toxicity of AZT which would be repeated in-vivo at the level of tissues and organs, which are, of course, comprised of individual cells.

The present invention extends to the use of one or more redox compounds with or without uridine (and functional derivatives or precursors thereof) and/or an anti-oxidant in the treatment of male infertility. Frequently, male infertility results from low or reduced motility of sperm. Such a low or reduced motility may result from a decline in bioenergy capacity. Accordingly, by treating a male patient in accordance with the present invention, the effects of the bioenergy deficiency can be ameliorated thereby permitting an increase in sperm motility.

The present invention is further described with reference to the following non-limiting Figures and Examples.

Figure 1B:
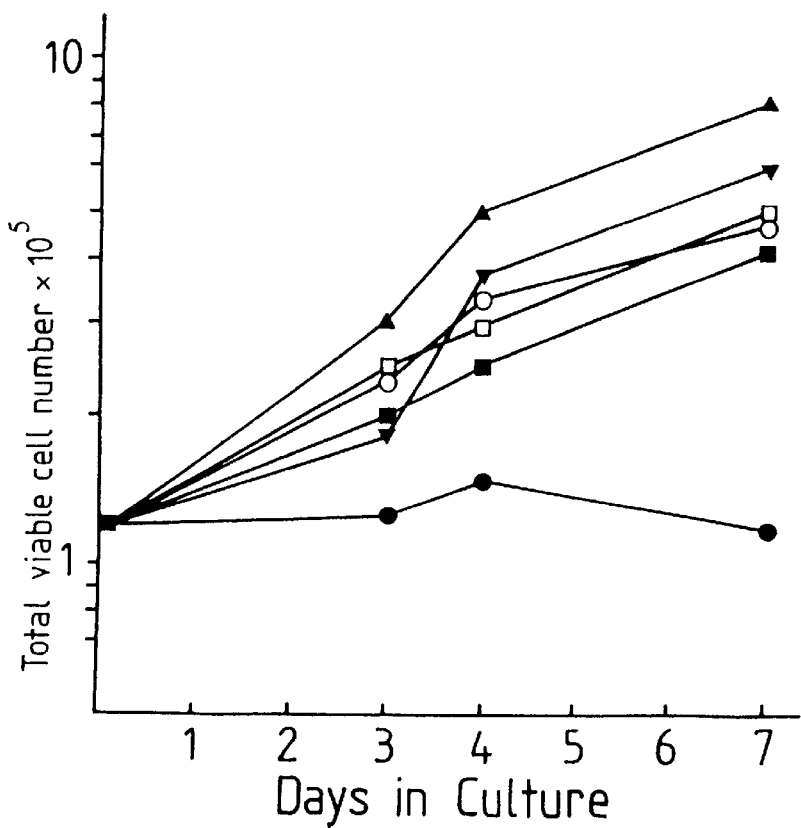

In the Figures:

FIG. 1 is a graphical representation showing the rescue of human $ρ°$ cells using redox compounds. Total viable cell number $(x10^5)$ is plotted against days in culture. (a) $ρ°$ cells were incubated with nutrient medium (●) and nutrient medium in the presence of pyruvate (▲), ferricyanide (■) and diferrictransferrin (○), (b) $ρ°$ cells were incubated with nutrient medium (●), $Q_{10}$ (▲), $Q_{10c}$ (▼), $Q_{6c}$ (■), $Q_{4c}$ (□) and $Q_{3c}$ (○) and $Q_6$ (○).

Figure 2:
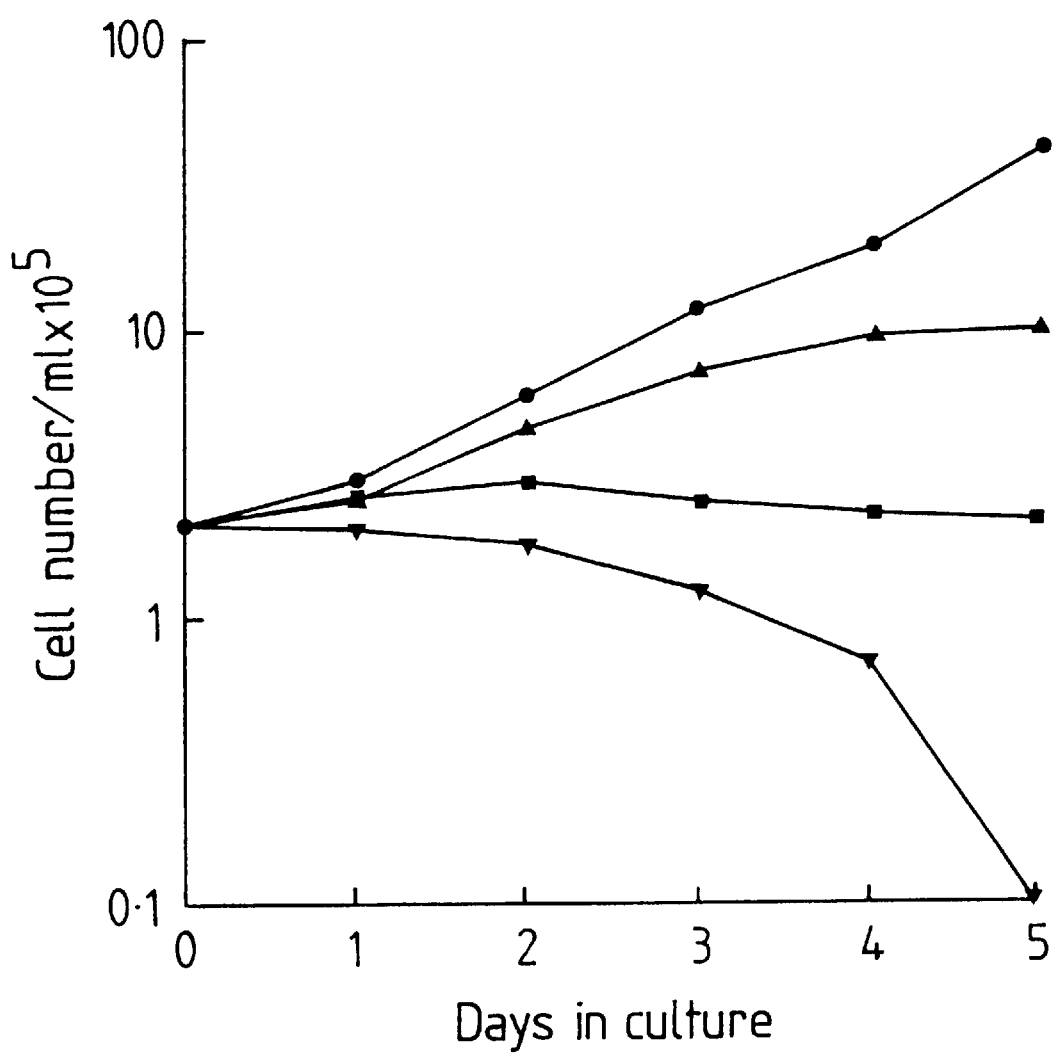

FIG. 2 is a graphical representation showing the effect of AZT on the growth of human Namalwa cells. Cell number per ml $(x10^5)$ is plotted against days in culture. Cells were incubated in the absence of AZT (●control) and in the presence of 10 μg/ml AZT (▲), 100 μg/ml AZT (■) and 500 μg/ml AZT (▼).

Figure 3:
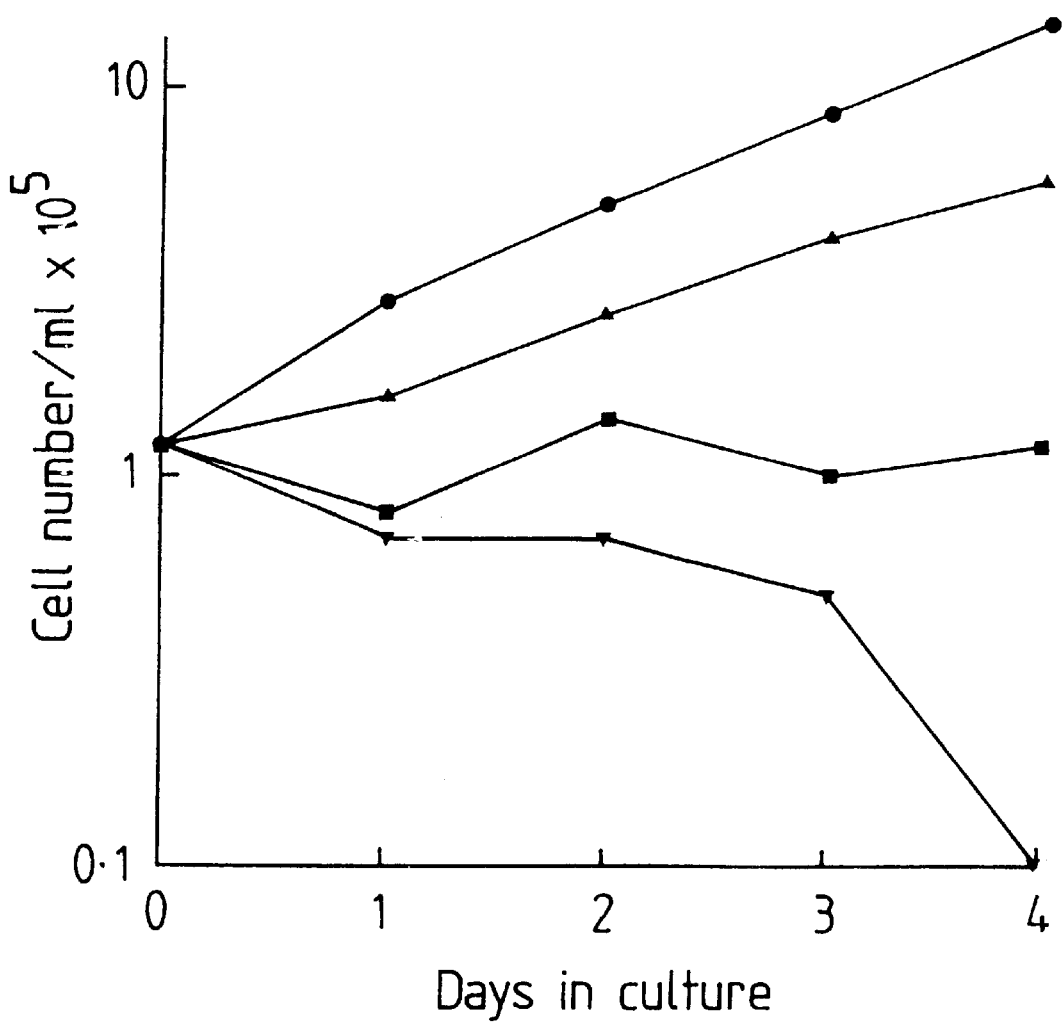

FIG. 3 is a graphical representation showing the effect of AMT on the growth of human Namalwa cells. Cell number per ml $(x10^5)$ is plotted against days in culture. Cell were incubated in the absence of AMT (●control) and in the presence of 1 μg/ml AMT (▲), 10 μg/ml AMT (■) and 100 μg/ml AMT (▼).

Figure 4:
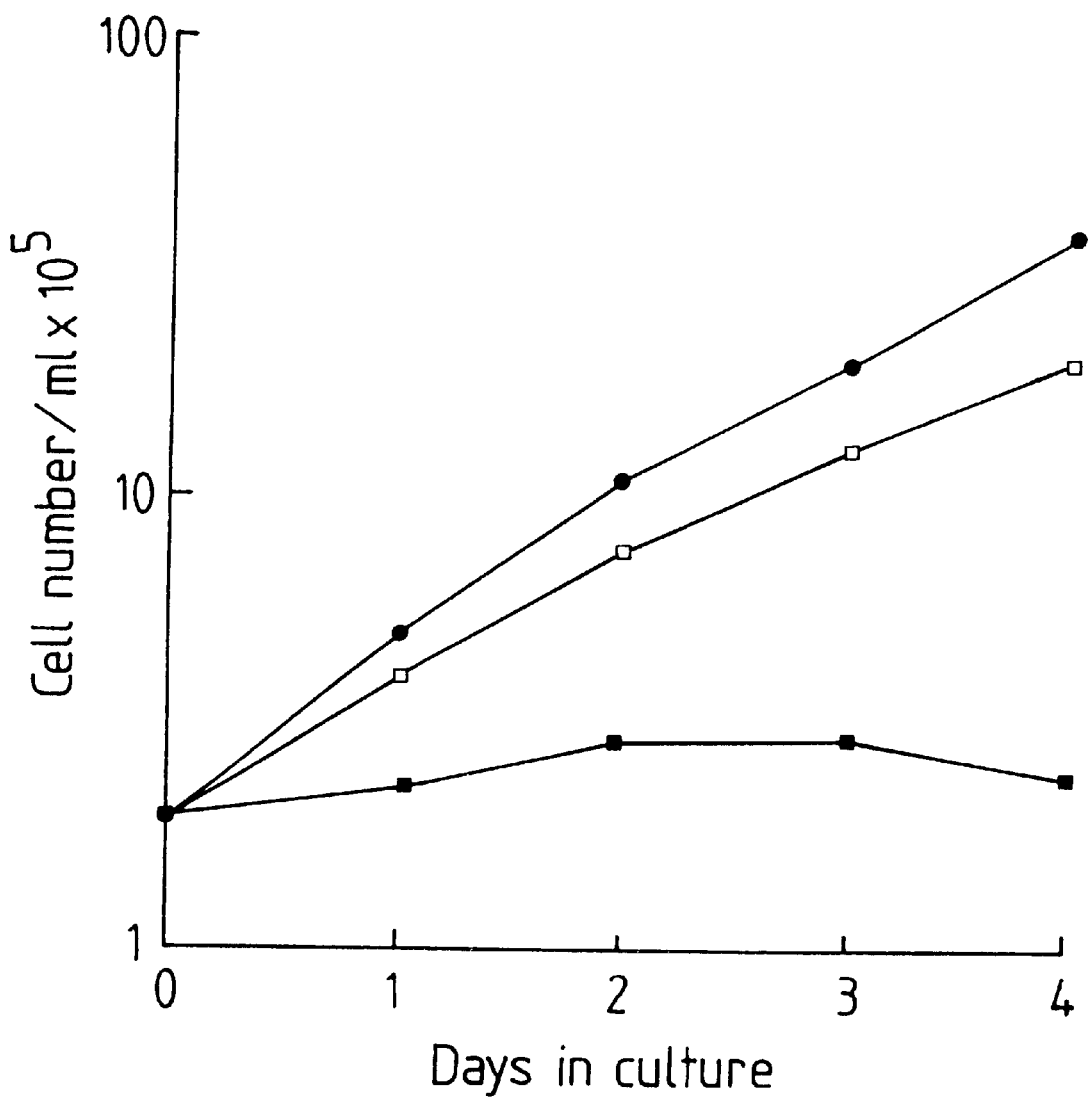

FIG. 4 is a graphical representation showing $Q_{10}$ redox-rescue of human Namalwa cells grown in the presence of AZT. Cell number per ml (x10$^5$) is plotted against days of culture. Cells were incubated in the absence of AZT (●control), in 100 μg/ml AZT and 10 μg/ml $Q_{10}$ (□), and 100 μg/ml AZT (■).

Figure 5:
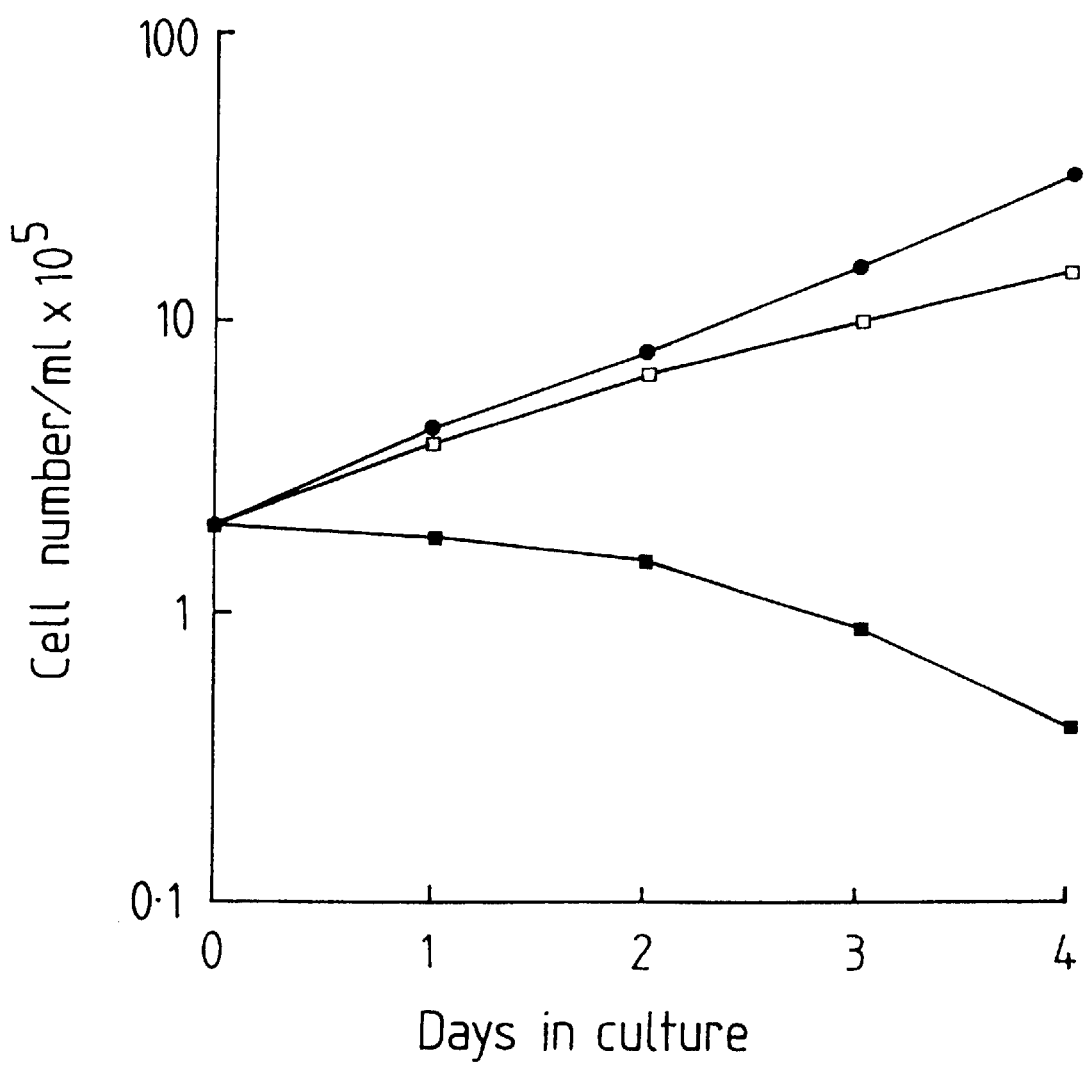

FIG. 5 is a graphical representation showing $Q_{10}$ redox-rescue of human Namalwa cells grown in the presence of AMT. Cell number per ml (x10$^5$) is plotted against days of culture. Cells were incubated in the absence of AMT (●control), in 100 μg/ml AMT and 10 μg/ml $Q_{10}$ (□), and 10 μg/ml AMT (■).

Figure 6:
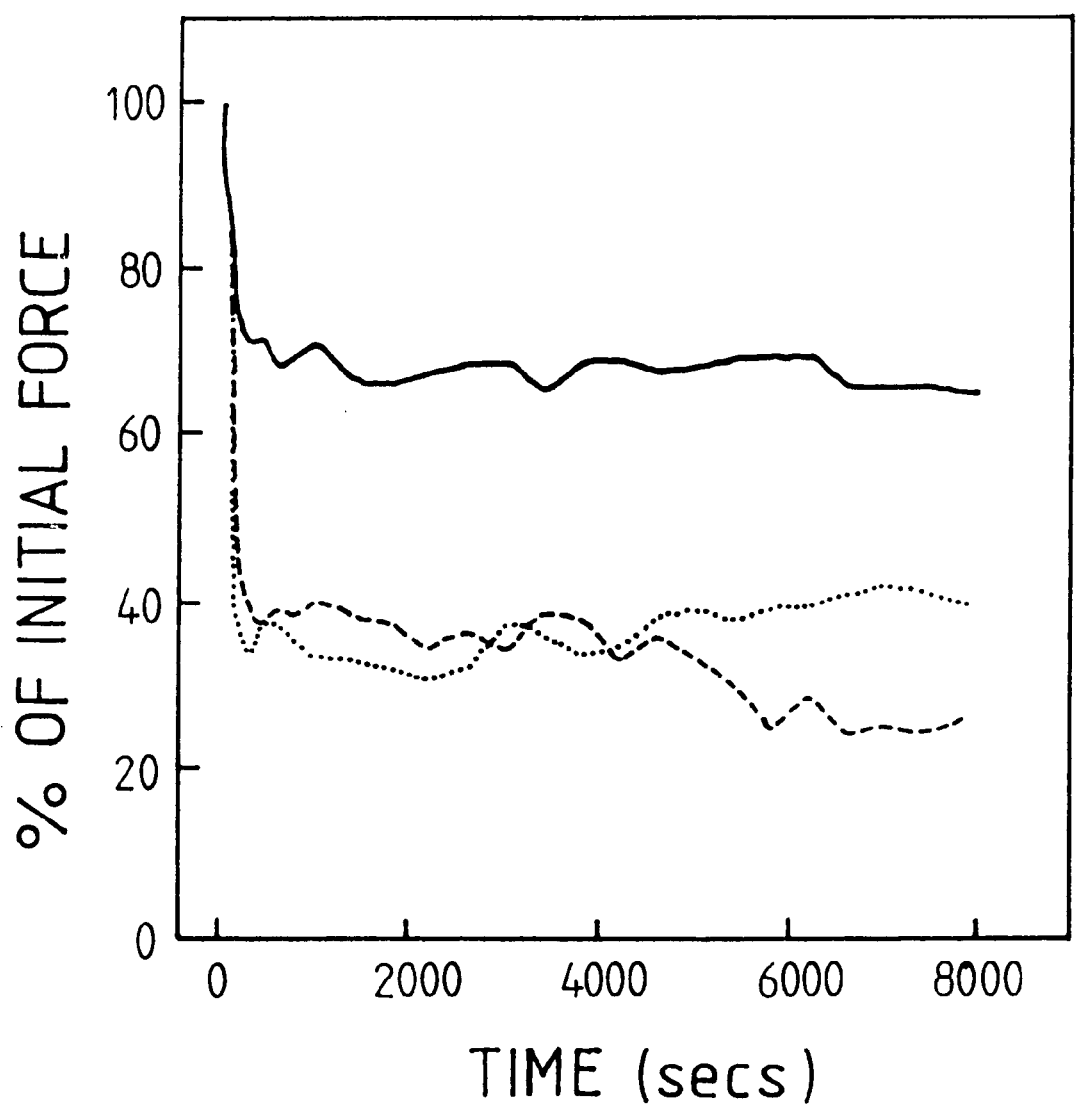

FIG. 6 is a graphical representation of mean fatigue profiles of soleus muscle from young adult (solid line, n=3), aged (dashed line, n=10) and aged $Q_{10}$ treated (dotted line, n=7) rats.

EXAMPLE 1

Human Namalwa cells were cultured in RPMI-1640 supplemented with 10% v/v fetal calf serum and supplemented with uridine (50 μg/ml). Pyruvate, ferricyanide diferrictransferrin, coenzymes $Q_{10}$, $Q_{10c}$, $Q_6$, $Q_{6c}$, $Q_{4c}$ and $Q_{3c}$ (hereinafter referred to as "$Q_{10}$", "$Q_{10c}$", "$Q_6$", "$Q_{6c}$", "$Q_{4c}$" and "$Q_{3c}$", respectively) were added to a final concentration of 1 mM, 100 μM, 10 μg/ml, 12 μM, 10 μM, 10 μM, 5 μM, 10 μM and 10 μM, respectively. Ferrocyanide may also be used which is converted to ferricyanide.

ρ° cells were obtained by long term treatment with ethidium bromide according to the methods of Desjardins et al. *Mol. Cell. Biol.*, 5, 1163–1169, 1985 and King and Attardi *Science*, 246, 500–503 1989.

As shown in FIG. 1, ρ° cells incubated in the presence of nutrient media were non-viable, showing no measurable increase in cell number over 7 days in culture. In distinct contrast, ρ° cells incubated with the redox compounds 100 μM ferricyanide and $Q_{10-Q3c}$, all showed significant growths of viable cells over the 7 day incubation period as a result of enhancement of cellular ATP levels by the aforementioned redox compounds.

Mammalian cells are impermeable to ferricyanide (Crane et al., *B.B.A.*, 811, 233–264, 1985 and, hence, the growth restorative action of ferricyanide in ρ° cells is likely to be mediated by an NADH-linked plasma membrane oxidoreductase which utilises this compound as an efficient external electron acceptor to generate cellular NAD$^+$ levels. Continuous restoration of appropriate intracellular NAD$^+$ levels is thus achieved by ferricyanide acting externally of the cell, this allowing glycolysis to provide ATP for the growth of mitochondrially respiratory incompetent ρ° cells.

The ability of $Q_{10}$ to allow ρ° cells to grow under aerobic conditions indicates that one mode of action of $Q_{10}$ may be to act as an electron acceptor for the plasma membrane-associated NADH dehydrogenase or oxidase. As respiratory electron transport is non-functional in ρ° cells, $Q_{10}$ and $Q_{3c}$ act as redox sinks to generate cytoplasmic NAD$^+$ (as does ferricyanide) because it cannot in this situation act as a by-pass reagent to restore impaired oxidative phosphorylation.

Mitochondrially impaired cell models as exemplified by the ρ° cells are a powerful tool for investigating cells which are bioenergy deficient. The restoration/increase of ATP production in these cells shows cellular ATP production may be increased in-vivo in animals. Thus, redox compounds may be used in the treatment of cells which are unable to meet their biological energy demand, and thus may be used in the treatment of ageing, in ameliorating the effects of mitochondrial toxic agents which disrupt mitochondrial oxidative phosphorylation, and in disease states associated with inoperative or malfunctioning mitochondrial oxidative phosphorylation.

EXAMPLE 2

Human Namalwa cells were cultured in RPMI-1640 growth medium as described in Example 1.

AZT and AMT were added to the growth media at various concentrations and the viable cells determined by trypan blue exclusion assay.

FIG. 2 shows the effect of AZT on the growth of Namalwa cells. Control cells divided in an exponential manner as expected on culture in nutrient media AZT at concentrations of 10 μg/ml 100 μg/ml and 500 μg/ml reduced the number of viable cells. At a concentration of 10 μg/ml cell number increased but began to plateau after 5 days in culture. At a concentration of 100 μg/ml AZT the number of cells in culture remained relatively constant. At 500 μg/ml AZT, there were no viable remaining cells after 5 days of culture and thus AZT showed marked cytotoxicity.

FIG. 3 shows the effect of incubating human Namalwa cells with AMT, a metabolite of AZT and also a possible impurity in AZT preparation. It is evident from FIG. 3, that AMT is highly toxic to cells in concentrations of 10 μg/ml and 100 μg/ml. Hence, by comparison with the data presented in FIG. 2, AMT is at least in order of magnitude more toxic than AZT.

FIG. 4 shows the amelioration of the toxic effect of AZT in human Namalwa cells. At a concentration of 100 μg/ml AZT, AZT was clearly cytotoxic. However, where the cells were incubated with 10 μg/ml $Q_{10}$ in combination with 100 μg/ml AZT, the toxic effect of AZT was ameliorated with a significant proportion of cells being scored as viable, this result being almost equivalent to control cells incubated in the absence of AZT.

Similar results to FIG. 4 are shown in FIG. 5 where the redox compound $Q_{10}$ ameliorates the cytotoxic effect of AMT on Namalwa cells. AMT at 10 μg/ml is highly cytotoxic to cells. However, in the presence of 10 μg/ml $Q_{10}$ the cytotoxic effects of 10 μg/ml of AMT are reversed or ameliorated such that Namalwa cells divide and remain viable in culture in a manner similar to control cells incubated in the absence of AMT.

Examples of redox compounds within the scope of Formulae (I)–(IV) and useful in accordance with the present invention are shown in Examples 3–14 hereinafter.

EXAMPLE 3

2,3-Dimethoxy-5-methyl-6-prop-2'-enyl-1,4-benzoquinone

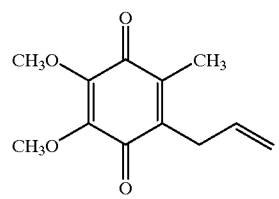

EXAMPLE 4

2,3-Dimethoxy-5-methyl-6-(1'-methoylprop-2'-enyl)-1,4-benzoquinone

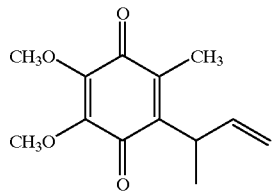

EXAMPLE 5

6-(E)-Butanol-enyl-2,3-dimethoxy-5-methyl-1,4-benzoquinone

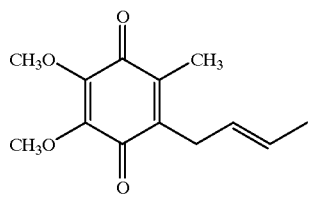

EXAMPLE 6

2,3-Dimethoxy-5-methyl-6-(3'-methylbut-2'-enyl)-1,4-benzoquinone

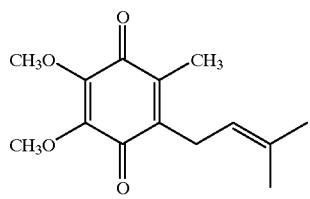

EXAMPLE 7

2,3-Dimethoxy-5-methyl-6-(2'-(E),4'-(E)-1'-methylpenta-2',4'-dienyl)-1,4-benzoquinone

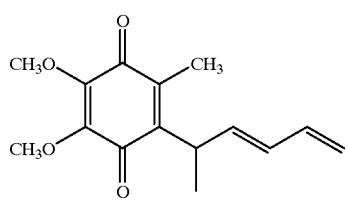

EXAMPLE 8

2,3-Dimethoxy-6-(2'-(e),4'-(e)-hexa-2',4'-dienyl)-5-methyl-1,4-benzoquinone

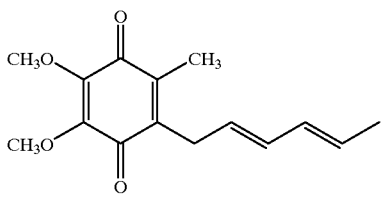

EXAMPLE 9

2,3-Dimethoxy-5-methyl-6-propyl-1,4-benzoquinone

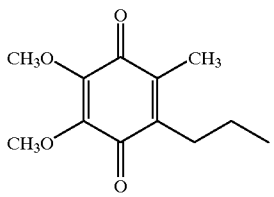

EXAMPLE 10

2,3-Dimethoxy-6-hexyl-5-methyl-1,4-benzoquinone

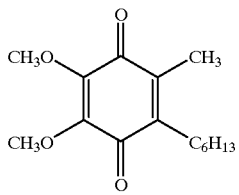

EXAMPLE 11

2,3-Dimethoxy-5-methyl-6-nonyl-1,4-benzoquinone

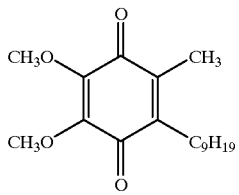

EXAMPLE 12

6-Decyl-2,3-dimethoxy-5-methyl-1,4benzoquinone

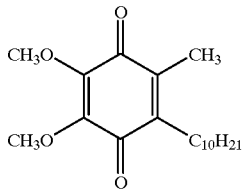

EXAMPLE 13

Ubiquinone-6

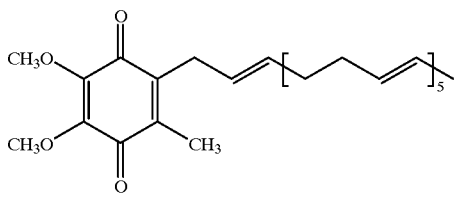

EXAMPLE 14

Ubiquinone-10

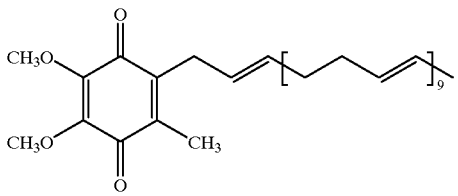

EXAMPLE 15

Compounds useful in accordance with the present invention can be treated in the following animal model.

Sprague-Dawley rats are used at approximately 26 months of age. Experiments are conducted using soleus muscle under in vivo conditions. This muscle is chosen because it contains 85–90% type I fibres and 10–15% type IIA fibres. Type I fibres are slow-twitch, with a high mitochondrial density and are normally highly resistant to fatigue, type IIA fibres are fast-twitch with a relatively high mitochondrial density and are also fatigue resistant. Another useful skeletal muscle is medial gastrocnemius, medial gastrocnemius, like soleus, is an ankle extensor but is of very different fibre type composition. It contains mainly type IIA and IIB (fast-twitch and fatigable) fibres and a small proportion of type I fibres. Soleus, therefore, provides an example of a very fatigue resistant skeletal muscle, whereas medial gastrocnemius is more typical of the majority of muscles in the body.

Both soleus and medial gastrocnemius is investigated in vivo in the anaesthetised rat (4 ml/kg body weight urethane in a 25% w/v solution, freshly prepared i.p.). The muscle is stimulated via its nerve with the blood supply intact at a temperature of 35° C. Recording conditions are isometric with the muscle set at optimum length. The basic isometric contractile characteristics are determined and the muscle then stimulated at 40 Hz for 33 ms every second (i.e. duty cycle one third of a second stimulated, two thirds rest) for periods up to 8,000 seconds. The contractile responses and the muscle electromyographic (EMG) signal are recorded on tape and selected records are captured on line with a computer based data logging system.

EXAMPLE 16

To determine the diminution in endurance and functional capacity with age in the animal model a comparison is made betwen muscles from young adult animals six months old and aged animals (about 26 months).

Preliminary results (FIG. 6) indicate that following prolonged repetitive stimulation (40 Hz, 330 ms every second) for periods in excess of two hours, force developed by young adult rat soleus muscle declined rapidly to approximately 70% of its initial force. This level of force is then maintained for the duration of stimulation. However, in the aged animal the initial decline in force is much greater (approximately 40% of initial force) and thereafter continued to decline. Results obtained from 24 to 26 month-old rats treated with coenzyme $Q_{10}$ by daily i.p. injections for a period of 4 weeks show that co-enzyme $Q_{10}$ though unable to prevent the initial decline in force was able to successfully prevent the progressive decline in force (FIG. 6). In this experiment, $Q_{10}$ is administered at a dose level of 2 mg/kg/day in the presence of solvent/emulsifier HCO-60 solvent, which corresponds to the oral dosage level received by human mitochondrial disease patients. The i.p. route of administration is used in preference to the oral route to ensure that a high absorption of the compound is achieved.

EXAMPLE 17

In a preliminary experiment, the inventors have shown that administering AZT by i.p. injection at a dose level of 10 mg/kg/day (corresponding to the oral dosage level given to HIV positive and AIDS patients) for a period of 4 weeks almost completely abolished the contractile response of the soleus muscle to repetitive stimulation. Although the animals appeared normal and were able to feed and groom themselves. To further investigate the effect of AZT treatment on the decline in skeletal muscle performance, rats are treated concomitantly with co-enzyme $Q_{10}$ (2 mg/kg/day) and AZT (10 mg/kg/day). The response of skeletal muscle is investigated at 1, 2 and 4 weeks, respectively. A further group of rats receives $Q_{10}$ alone for 4 weeks prior respectively. Animals also receive AZT and HCO-60 ($Q_{10}$ carrier) for periods of 1, 2 and 4 weeks, respectively and serve as the control group for the first two groups.

EXAMPLE 17

In a further related experiment rats were exposed to AZT over an approximately 90 day period and mean soleus fatigue profiles determined. The results are graphically shown below. AZT (10 mg/kg) was administered as described in Example 17 to 6 month old rats and the percentage of initial force determined over time. Rats which received AZT and a solvent/emulsifier (HCO-60) showed a significant decline relative to control rats which did not receive any treatment. However, rats which received both AZT and a redox compound (co-enzyme $Q_{10c}$; Example 12) behaved in a similar manner to the control rats. The results show the ameliorating effects of $Q_{10c}$ on the functional debilitation caused by AZT treatment.

Mean Soleus Fatigue Profiles of Rats Treated with AZT

Ameliorating Effects of Concomitant Treatment with $Q_{10c}$

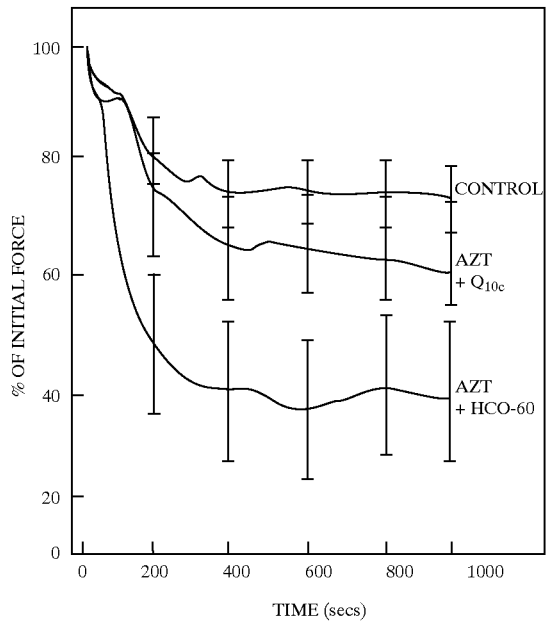

EXAMPLE 18

It is contemplated in accordance with the present invention that treatment of patients with redox compounds either before or during the induced ischaemia of cardiac surgery improves the tolerance of the senescent myocardium to ischaemia and to reperfusion. Induced arrest (cardioplegia) during cardiac surgery causes a reduction in oxygen consumption, metabolic efficiency and enegy supply during the post-cardioplegic recovery period.

To determine whether treatment with redox compounds, either before or during induced ischaemia might improve the tolerance of the senscent myocardium to ischaemic injury. It may be carried out in rat hears perfused with Kreb's buffer on the isolated working heart apparatus. If protective effect of a particular agent is identified, this agent is then tested further in young and old greyhound dogs perfused with blood on the heart-lung machine as used during open heart surgery.

Human cardiac tissue may also be studied. A recent development permits the preparation of thin myocardial strips from human and artrial wall, atrial trabeculae and from papillary muscles, that can be used for assessment of myocardial contractile function. A key to the successful application of such small scale muscle preparations (Mulieri et al Circul. Res. 65; 1441–1444, 1989) is the use of 2,3-butanedione monoxime (BDM), which functionally and structurally protects the cardiac tissues during dissection, permitting the isolation of functional human myocardial strips of less than 1 mm$^2$ in cross section. These strips can be mounted in an organ bath, then connected to a force transducer and stimulated electrially to induce contraction. These strips can then, under controlled conditions, be subjected to various stresses including hypoxia and high work loads induced by rapid electrical stimulation. In accordance with the present invention, the efficacy of redox compounds, with or without anti-oxidants and/or uridine (or its derivative or precursor), included in the organ bath, can be assessed on myocardial strips subjected to these stresses.

Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combinations of any two or more of said steps or features.

We claim:

1. A method for enhancing cellular bioenergy in an animal suffering from bioenergetic disease resulting from mitochondrially compromised cells, said method comprising administering to said animal uridine or a functional derivative or precursor thereof and a redox compound of Formula (I) having the structure:

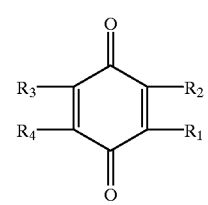

(I)

wherein $R_1$, $R_2$, $R_3$ and $R_4$ may be the same or different and $R_1$ is H, $C_1$–$C_{10}$ alkyl, $C_1$–$C_{10}$ alkoxy, $C_2$–$C_{10}$ alkenyl, $C_2$–$C_{10}$ alkynyl, $C_3$–$C_{10}$ cycloalkyl, $C_1$–$C_{10}$ alkylthio, $C_1$–$C_{10}$ haloalkyl, phenyl, phenoxy, or thiophenoxy, each of which may be either unsubstituted or substituted with a substituent from the group consisting of halogen, $C_1$–$C_6$ alkyl, $C_1$–$C_6$ alkoxy, alkylthio, amino, $C_1$–$C_6$ haloalkyl and $C_1$–$C_5$ haloalkoxy; or $$R_1 \text{ is } (CH_{\overline{n}}-CH_{n1}-\overset{R_5}{\underset{|}{C}}H_{n2}-\overset{R_6}{\underset{|}{C}}H_{n3})_{n4}$$

wherein
  n and $n_1$ are independently either 1 or 2;
  $n_2$ is 0 or 1;
  $n_3$ is either 1 or 2;
  $n_4$ is 1–40; and
wherein
  $R_5$ and $R_6$ may be the same or different and each is H, $C_1$–$C_{10}$ alkyl, $C_1$–$C_{10}$ alkoxy, $C_2$–$C_{10}$ alkynyl, $C_3$–$C_{10}$ cycloalkyl, $C_1$–$C_{10}$ alkylthio, $C_1$–$C_{10}$ haloalkyl, phenyl, phenoxy, or thiophenoxy, each of which may be either unsubstituted or substituted with a substituent selected from the group consisting of halogen, $C_1$–$C_6$ alkyl, $C_1$–$C_6$ alkoxy, alkylthio, amino, $C_1$–$C_6$ haloalkyl and $C_1$–$C_5$ haloalkoxy;
  where $R_2$, $R_3$ and $R_4$ each is selected from H, $C_1$–$C_{10}$ alkyl, $C_1$–$C_{10}$ alkoxy, $C_2$–$C_{10}$ alkenyl, $C_2$–$C_{10}$ alkynyl, $C_3$–$C_{10}$ cycloalkyl, $C_1$–$C_{10}$ alkylthio, $C_1$–$C_{10}$ haloalkyl, phenyl, phenoxy, or thiophenoxy, each of which may be either unsubstituted or substituted with a substituent from the group consisting of halogen, $C_1$–$C_6$ alkyl, $C_1$–$C_6$ alkoxy, alkylthio, amino, $C_1$–$C_6$ haloalkyl and $C_1$–$C_5$ haloalkoxy; and said compound being capable of replacing ferricyanide in the enablement of propagative aerobic growth of cultured ρ° cells of vertebrate origin in the absence of pyruvate.

2. The method according to claim 1 wherein the animal is a mammal selected from the group consisting of a human, livestock animal, laboratory test animal, companion animal and captive or free wild animal.

3. The method according to claim 1 wherein the animal is a human.

4. The method according to claim 1 wherein $R_1$ is

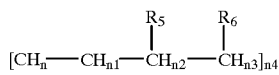

wherein n and $n_1$ are independently 1 or 2; $n_2$ is 0 or 1; $n_3$ is 1 or 2; and $n_4$ is 1–40 and wherein $R_5$ and $R_6$ may be the same or different and each is H, $C_1$–$C_{10}$ alkyl, $C_1$–$C_{10}$ alkoxy, $C_2$–$C_{10}$ alkynyl, $C_3$–$C_{10}$ cycloalkyl, $C_1$–$C_{10}$ alkylthio, $C_1$–$C_{10}$ haloalkyl, phenyl, phenoxy, or thiophenoxy, each of which may be either unsubstituted or substituted from the group consisting of halogen, $C_1$–$C_6$ alkyl, $C_1$–$C_6$ alkoxy, alkylthio, amino, $C_1$–$C_6$ haloalkyl and $C_1$–$C_5$ haloalkoxy.

5. A method for enhancing cellular bioenergy in an animal suffering from bioenergetic disease resulting from mitochondrially compromised cells, said method comprising administering to said animal uridine or a functional derivative or precursor thereof and a redox compound having the structure

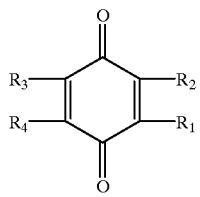

wherein $R_2$ is H or methyl;

$R_3$ and $R_4$ are the same or different and each is methyl or methoxy: and $R_1$ is [CH$_n$—CH$_{n_1}$—CH$_{n_2}$—CH$_{n_3}$]$_{n_4}$ with $R_5$ and $R_6$ substituents wherein n and $n_1$ are independently 0, 1 or 2; $n_2$ is 0 or 1; $n_3$ is 0, 1, or 2; and $n_4$ is 1–40 and $R_6$ is H and $R_5$ is $C_1$–$C_{10}$ alkyl, $C_2$–$C_{10}$ alkynyl, $C_1$–$C_{10}$ alkoxy or $C_2$–$C_{10}$ alkenyl, said compound being capable of replacing ferricyanide in the enablement of propagative aerobic growth of cultured ρ° cells of vertebrate origin in the absence of pyruvate.

6. A method for enhancing cellular bioenergy in an animal suffering from bioenergetic disease resulting from mitochrondrially compromised cells, said method comprising administration to said animal uridine or a functional derivative or precursor thereof and a redox compound having the structure:

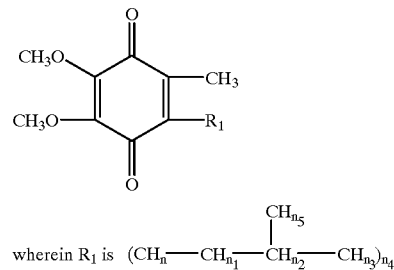

wherein $R_1$ is (CH$_n$—CH$_{n_1}$—CH$_{n_2}$—CH$_{n_3}$)$_{n_4}$ with CH$_{n_5}$ substituent where n is 1 or 2; $n_1$ is 1 or 2; $n_2$ is 0 or 1; $n_3$ is 2 or 3;

$n_4$ is 1–40; and $n_5$ is 2 or 3, said compound being capable of replacing ferricyanide in the enablement of propagative aerobic growth of cultured ρ° cells of vertebrate origin in the absence of pyruvate.

7. A method for enhancing cellular bioenergy in an animal suffering from bioenergetic disease resulting from mitochondrially compromised cells, said method comprising administrating to said animal uridine or a functional derivative or precursor thereof and a redox compound having the structure

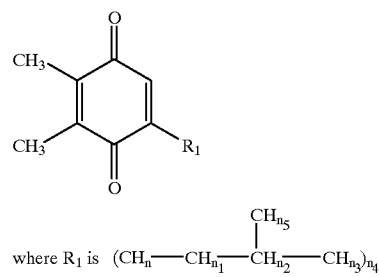

where $R_1$ is (CH$_n$—CH$_{n_1}$—CH$_{n_2}$—CH$_{n_3}$)$_{n_4}$ with CH$_{n_5}$ substituent wherein n is 1 or 2;

$n_1$ is 1 or 2;

$n_2$ is 0 or 1;

$n_3$ is 2 or 3;

$n_4$ is 1–40; and $n_5$ is 2 or 3, said compound being capable of replacing fericyanide in the enablement of propagative aerobic growth of cultured ρ° cells of vertebrate origin in the absence of pyruvate.

8. The method according to claim 1 wherein the effective amount of redox compound is from about 10 μg to about 50 mg per kilogram body weight per day.

9. The method according to claim 8 wherein the effective amount of redox compound is from about 100 μg to about 15 mg per kilogram body weight per day.

10. The method according to claim 1 further comprising the administration of an effective amount of an anti-oxidant.

11. The method according to claim 1 for ameliorating the effects of reduced bioenergetic capacity in diseases associated with aging, systemic or vascular disease or chemical therapy.

12. A pharmaceutical composition comprising a therapeutically effective amount of a redox compound of Formula (I) having the structure:

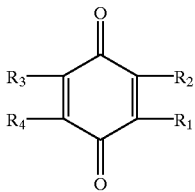
(I)

wherein $R_1$, $R_2$, $R_3$ and $R_4$ may be the same or different and $R_1$ is H, $C_1$–$C_{10}$ alkyl, $C_1$–$C_{10}$ alkoxy, $C_2$–$C_{10}$ alkenyl, $C_2$–$C_{10}$ alkynyl, $C_3$–$C_{10}$ cycloalkyl, $C_1$–$C_{10}$ alkylthio, $C_1$–$C_{10}$ haloalkyl, phenyl, phenoxy, or thiophenoxy, each of which may be either unsubstituted or substituted with a substituent selected from the group consisting of halogen, $C_1$–$C_6$ alkyl, $C_1$–$C_6$ alkoxy, alkylthio, amino, $C_1$–$C_6$ haloalkyl and $C_1$–$C_5$ haloalkoxy; or

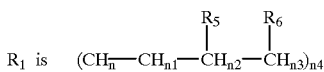
$R_1$ is $(CH_n$—$CH_{n1}$—$CH_{n2}$—$CH_{n3})_{n4}$ wherein
n and $n_1$ are independently either 1 or 2;
$n_2$ is 0 or 1;
$n_3$ is either 1 or 2;
$n_4$ is 1–40; and
wherein
$R_5$ and $R_6$ may be the same or different and each is H, $C_1$–$C_{10}$ alkyl, $C_1$–$C_{10}$ alkoxy, $C_2$–$C_{10}$ alkynyl, $C_3$–$C_{10}$ cycloalkyl, $C_1$–$C_{10}$ alkylthio, $C_1$–$C_{10}$ haloalkyl, phenyl, phenoxy, or thiophenoxy, each of which may be either unsubstituted or substituted with a substituent selected from the group consisting of halogen, $C_1$–$C_6$ alkyl, $C_1$–$C_6$ alkoxy, alkylthio, amino, $C_1$–$C_6$ haloalkyl and $C_1$–$C_5$ haloalkoxy;
where $R_2$, $R_3$ and $R_4$ each is selected from H, $C_1$–$C_{10}$ alkyl, $C_1$–$C_{10}$ alkoxy, $C_2$–$C_{10}$ alkenyl, $C_2$–$C_{10}$ alkynyl, $C_3$–$C_{10}$ cycloalkyl, $C_1$–$C_{10}$ alkylthio, $C_1$–$C_{10}$ haloalkyl, phenyl, phenoxy, or thiophenoxy, each of which may be either unsubstituted or substituted with a substituent from the group consisting of halogen, $C_1$–$C_6$ alkyl, $C_1$–$C_6$ alkoxy, alkylthio, amino, $C_1$–$C_6$ haloalkyl and $C_1$–$C_5$ haloalkoxy, said compound being capable of replacing ferricyanide in the enablement of propagative aerobic growth of cultured $\rho°$ cells of vertebrate origin in the absence of pyruvate; and uridine or a functional derivative and/or precursor thereof, and one or more pharmaceutically acceptable carriers and/or diluents.

13. The composition according to claim 12 wherein

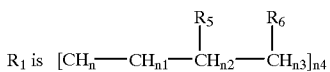
$R_1$ is $[CH_n$—$CH_{n1}$—$CH_{n2}$—$CH_{n3}]_{n4}$ wherein n and $n_1$ are independently 1 or 2; $n_2$ is 0 or 1; $n_3$ is 1 or 2; and
$n_4$ is 1–40 and
wherein $R_5$ and $R_6$ may be the same or different and each is H, $C_1$–$C_{10}$ alkyl, $C_1$–$C_{10}$ alkoxy, $C_2$–$C_{10}$ alkynyl, $C_3$–$C_{10}$ cycloalkyl, $C_1$–$C_{10}$ alkylthio, $C_1$–$C_{10}$ haloalkyl, phenyl, phenoxy, or thiophenoxy, each of which may be either unsubstituted or substituted by a substituent selected from the group consisting of halogen, $C_1$–$C_6$ alkyl, $C_1$–$C_6$ alkoxy, alkylthio, amino, $C_1$–$C_6$ haloalkyl and $C_1$–$C_5$ haloalkoxy.

14. A pharmaceutical composition comprising a therapeutically effective amount of a redox compound having the structure:

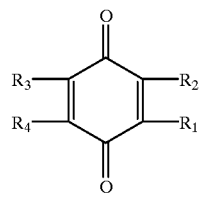

wherein
$R_2$ is H or methyl;
$R_3$ and $R_4$ are the same or different and each is methyl or methoxy; and

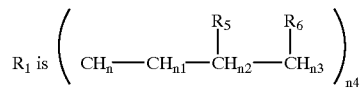
$R_1$ is $\left( CH_n\text{—}CH_{n1}\text{—}CH_{n2}\text{—}CH_{n3} \right)_{n4}$ n and $n_1$ are independently 1 or 2;
$n_2$ is 0 or 1;
$n_3$ is 1 or 2;
$n_4$ is 1–40;
$R_6$ is H; and
$R_8$ is $C_1$–$C_{10}$ alkyl, $C_2$–$C_{10}$ alkynyl, $C_1$–$C_{10}$ alkoxy or $C_2$–$C_{10}$ alkenyl,
and uridine or a functional derivative or a precursor thereof and one or more pharmaceutically acceptable carriers and/or diluents,
whereby said redox compound is capable of replacing ferricyanide in the enablement of propagative aerobic growth of cultured $\rho°$ cells of vertebrate origin in the absence of pyruvate.

15. A pharmaceutical composition comprising a therapeutically effective amount of a redox compound having the structure:

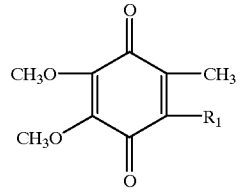

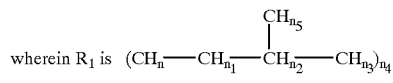
wherein $R_1$ is $(CH_n$—$CH_{n1}$—$CH_{n2}$—$CH_{n3})_{n4}$ where n is 1 or 2; $n_1$ is 1 or 2; $n_2$ is 0 or 1; $n_3$ is 2 or 3; $n_4$ is 1–40 and $n_5$ is 2 or 3,
and uridine or a functional derivative or a precursor thereof and one or more pharmaceutically acceptable carriers and/or diluents,
whereby said redox compound is capable of replacing ferricyanide in the enablement of propagative aerobic growth of cultured ρ° cells of vertebrate origin in the absence of pyruvate.

16. A pharmaceutical composition comprising a therapeutically effective amount of a redox compound having the structure:

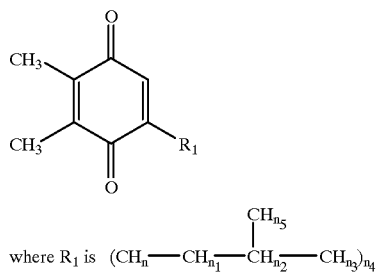

where $R_1$ is $(CH_n-CH_{n_1}-CH_{n_2}(CH_{n_5})-CH_{n_3})_{n_4}$ wherein n is 1 or 2; $n_1$ is 1 or 2; $n_2$ is 0 or 1; $n_3$ is 2 or 3; $n_4$ is 1–40; and $n_5$ is 2 or 3, and uridine or a functional derivative or a precursor thereof and one or more pharmaceutically acceptable carriers and/or diluents, whereby said redox compound is capable of replacing ferricyanide in the enablement of propagative aerobic growth of cultured ρ° cells of vertebrate origin in the absence of pyruvate.

17. The method according to claim 11 wherein the disease is heart disease, a neurological or muscular disorder or diabetes.

18. The method according to claim 10 wherein the anti-oxidant is Vitamin C or Vitamin E.

19. The method according to claim 1 wherein orotic acid and said redox compound are administered to said animal.

20. The method according to claim 1 wherein uridine and said redox compound are administered to said animal.

21. The pharmaceutical composition according to claim 12 further comprising Vitamin C or Vitamin E.

22. The pharmaceutical composition according to claim 12 comprising a therapeutically effective amount of said redox compound and uridine and a pharmaceutically acceptable carrier therefor.

23. The pharmaceutical composition according to claim 12 comprising a therapeutically effective amount of said redox compound and orotic acid and a pharmaceutically acceptable carrier therefor.

24. The pharmaceutical composition according to claim 21 further comprising an anti-retroviral agent.

25. The pharmaceutical composition according to claim 24 wherein the anti-retroviral agent is AZT.

* * * * *

UNITED STATES PATENT AND TRADEMARK OFFICE
CERTIFICATE OF CORRECTION

PATENT NO.    : 5,981,601
DATED         : November 9, 1999
INVENTOR(S)   : Philip Nagly et al.

It is certified that error appears in the above-identified patent and that said Letters Patent is hereby corrected as shown below:

Title page,
Item [30], "2641/92" and "2642/92" should read -- PL2641/92 -- and -- PL2642/92 --.

Column 2,
Line 61, after "animal" insert -- . --

Column 4,
Line 6, after "described" insert -- . --
Line 33, "$CC_1$" should read -- $C_1$ --
Line 44, "$C_{1\text{-}C_{10}}$" should read -- $C_1$ - $C_{10}$ --

Column 6,
Lines 41-42, after "treatment" insert -- . --

Column 12,
Line 14, "2shows" should read -- 2 shows --

Column 13,
Line 56, both instances of "(E)" should read -- (E) --

Column 14,
Line 5, both instances of "(e)" should read -- (e) --

Column 15,
Line 3, after "4" insert -- - --

UNITED STATES PATENT AND TRADEMARK OFFICE
CERTIFICATE OF CORRECTION

PATENT NO. : 5,981,601
DATED : November 9, 1999
INVENTOR(S) : Philip Nagly et al.

It is certified that error appears in the above-identified patent and that said Letters Patent is hereby corrected as shown below:

Column 16,
Line 29, delete "solvent/"
Line 54, "17" should read -- 17A --

Column 17,
Line 2, "AZT" should read -- AZT: --

Signed and Sealed this

Second Day of December, 2003

JAMES E. ROGAN
*Director of the United States Patent and Trademark Office*